(12) United States Patent
Jeon et al.

(10) Patent No.: US 10,031,172 B2
(45) Date of Patent: Jul. 24, 2018

(54) METHOD AND APPARATUS FOR DETERMINING OCCURRENCE OF ELECTRICAL FAULT IN CHANNEL OF ULTRASOUND PROBE

(71) Applicant: SAMSUNG MEDISON CO., LTD., Hongcheon-gun (KR)

(72) Inventors: Tae-ho Jeon, Seoul (KR); Jong-keun Song, Yongin-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 127 days.

(21) Appl. No.: 15/172,839

(22) Filed: Jun. 3, 2016

(65) Prior Publication Data
US 2017/0160329 A1    Jun. 8, 2017

(30) Foreign Application Priority Data
Dec. 4, 2015 (KR) .................. 10-2015-0172655

(51) Int. Cl.
| | | |
|---|---|---|
| G01R 31/02 | (2006.01) |
| G01N 29/24 | (2006.01) |
| B06B 1/02 | (2006.01) |
| G01S 7/52 | (2006.01) |
| A61B 8/06 | (2006.01) |

(Continued)

(52) U.S. Cl.
CPC ............ G01R 31/02 (2013.01); A61B 8/4483 (2013.01); A61B 8/58 (2013.01); B06B 1/0207 (2013.01); G01N 29/24 (2013.01); G01S 7/5205 (2013.01); A61B 8/06 (2013.01); A61B 8/4405 (2013.01); A61B 8/4472 (2013.01); A61B 8/483 (2013.01); A61B 8/488 (2013.01); A61B 8/565 (2013.01)

(58) Field of Classification Search
CPC ...... G01R 31/00; G01R 31/002; G01R 31/02; G01R 31/024; G01R 31/025; G01R 31/08; G01R 31/28; G01R 31/31924; G01N 29/24; G01S 7/5205; A61B 8/06; A61B 8/4405; A61B 8/4472; A61B 8/483; A61B 8/488; A61B 8/565; A61B 8/58; A61B 8/4483; B06B 1/0207
USPC ............... 324/500, 509, 511, 512, 522, 537, 324/750.01, 754.01
See application file for complete search history.

(56) References Cited

U.S. PATENT DOCUMENTS

| | | | |
|---|---|---|---|
| 3,710,792 A | * | 1/1973 | Light .................... A61B 8/06 600/457 |
| 5,517,994 A | | 5/1996 | Burke et al. |

(Continued)

FOREIGN PATENT DOCUMENTS

| | | |
|---|---|---|
| JP | 2006-095291 A | 4/2006 |
| JP | 2008-136725 A | 6/2008 |

(Continued)

OTHER PUBLICATIONS

Communication dated Apr. 18, 2017 by the European Patent Office in counterpart European Patent Application No. 16169096.1.

Primary Examiner — Hoai-An D Nguyen
(74) Attorney, Agent, or Firm — Sughrue Mion, PLLC

(57) ABSTRACT

Provided is a method of controlling an operation of a channel including at least one transducer, which includes comparing a voltage corresponding to current flowing into the channel to a threshold voltage and controlling the operation of the channel based on a result of the comparing.

16 Claims, 13 Drawing Sheets

(51) Int. Cl.
  *A61B 8/00*  (2006.01)
  *A61B 8/08*  (2006.01)

(56) References Cited

U.S. PATENT DOCUMENTS

| | | | |
|---|---|---|---|
| 8,143,898 B1* | 3/2012 | Markoff | A61B 6/583 |
| | | | 324/522 |
| 8,148,997 B2* | 4/2012 | Hofmayer | G01D 3/08 |
| | | | 324/537 |
| 9,237,882 B2 | 1/2016 | Kumazawa | |
| 2006/0145059 A1 | 7/2006 | Lee et al. | |
| 2012/0101379 A1 | 4/2012 | Katou | |
| 2014/0184383 A1 | 7/2014 | Wodnicki | |
| 2015/0071030 A1 | 3/2015 | Hayashi | |
| 2015/0157299 A1 | 6/2015 | Hopple et al. | |
| 2017/0184701 A1* | 6/2017 | Bharat | G01S 7/003 |
| 2017/0269039 A1* | 9/2017 | Bagge | G01N 29/24 |

FOREIGN PATENT DOCUMENTS

| | | |
|---|---|---|
| JP | 2012-011118 A | 1/2012 |
| JP | 2015-053961 A | 3/2015 |
| WO | 2007/028960 A1 | 3/2007 |

* cited by examiner

METHOD AND APPARATUS FOR DETERMINING OCCURRENCE OF ELECTRICAL FAULT IN CHANNEL OF ULTRASOUND PROBE

CROSS-REFERENCE TO RELATED APPLICATION

This application claims the benefit of Korean Patent Application No. 10-2015-0172655, filed on Dec. 4, 2015, in the Korean Intellectual Property Office, the disclosure of which is incorporated herein in its entirety by reference.

BACKGROUND

1. Field

The present disclosure relates to methods and apparatuses for determining an occurrence of an electrical fault in a channel of an ultrasound probe.

2. Description of the Related Art

Ultrasound diagnosis apparatuses transmit ultrasound signals generated by transducers of a probe to an object and receive information about echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

As the number of transducers arranged in a probe increases, the number of channels for transmitting and receiving ultrasound waves increases accordingly. Since each of the channels includes an electronic circuit, a leakage current may occur due to shorting of a transducer or a fault in internal circuitry of a channel. The leakage current causes a probe to malfunction.

In particular, in a two-dimensional (2D) matrix probe, a circuit for summing signals received via a plurality of channels is added to the probe for the purpose of reducing the number of output signals from the probe. Thus, it is difficult to determine whether a leakage current has occurred simply by checking an output signal or impedance.

SUMMARY

Provided are methods and apparatuses for determining an occurrence of an electrical fault in a channel of an ultrasound probe.

Provided is a non-transitory computer-readable recording medium having recorded thereon a program for executing the methods on a computer.

Additional aspects will be set forth in part in the description which follows and, in part, will be apparent from the description, or may be learned by practice of the presented embodiments.

According to an aspect of an embodiment, a method of controlling an operation of a channel including at least one transducer includes: comparing a voltage corresponding to current flowing into the channel to a threshold voltage; and controlling the operation of the channel based on a result of the comparing.

The controlling of the operation of the channel may include blocking flow of the current into the channel.

The controlling of the operation of the channel comprises blocking flow of the current into at least one element included in the channel.

The controlling of the operation of the channel may include blocking a signal generated by the channel from being output.

The channel may be included in a probe, and the probe may include a two-dimensional (2D) transducer array.

The comparing of the voltage may include converting the current flowing into the channel into the voltage and comparing the voltage to the threshold voltage.

The comparing of the voltage may be performed by a circuit including a converter and a comparator.

The method may further include outputting information about whether the current flowing into the channel is an abnormal current.

The outputting of the information may be performed by a circuit including a flip-flop.

According to an aspect of another embodiment, a non-transitory computer-readable recording medium has recorded thereon a program for executing the method on a computer.

According to an aspect of another embodiment, an apparatus for controlling an operation of a channel including at least one transducer includes a first circuit configured to compare a voltage corresponding to current flowing into the channel to a threshold voltage and a second circuit configured to control the operation of the channel based on a result of the comparing.

The second circuit may block flow of the current into the channel.

The second circuit may block flow of the current into at least one element included in the channel.

The second circuit may block output of a signal generated by the channel.

The channel may be included in a probe, and the probe may include a 2D transducer array.

The first circuit may convert the current flowing into the channel into the voltage and compare the voltage to the threshold voltage.

The first circuit may include a converter and a comparator.

The apparatus may further include a third circuit configured to output information about whether the current flowing into the channel is an abnormal current.

The third circuit may include a flip-flop.

According to an aspect of another embodiment, a probe connected to an ultrasound diagnosis apparatus includes a control circuit that is connected to channels, each channel including a group of transducers in the probe. The control circuit may include: a first circuit configured to compare a voltage corresponding to current flowing into the channel to a threshold voltage; a second circuit configured to control an operation of the channel based on a result of the comparing; and a third circuit configured to output information about whether the current flowing into the channel is an abnormal current to the ultrasound diagnosis apparatus.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "ultrasound image" refers to an image of an object, which is obtained using ultrasound waves, or an image showing a region of interest (ROI) included in the object. An ROI refers to a region of an object that a user desires to observe with more focused attention, and, for example, may be a region including a lesion. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, embodiments will be described in detail with reference to the accompanying drawings.

Figure 1A:
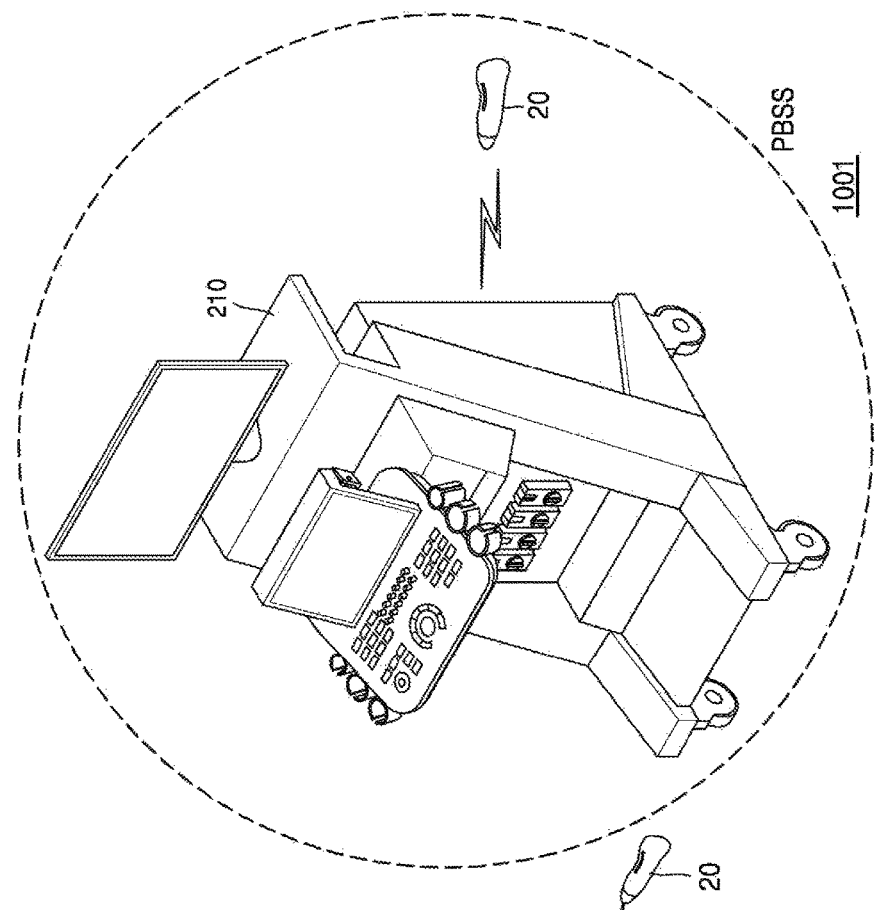
FIGS. 1A and 1B illustrate examples of ultrasound diagnosis systems according to embodiments.
Figure 1B:
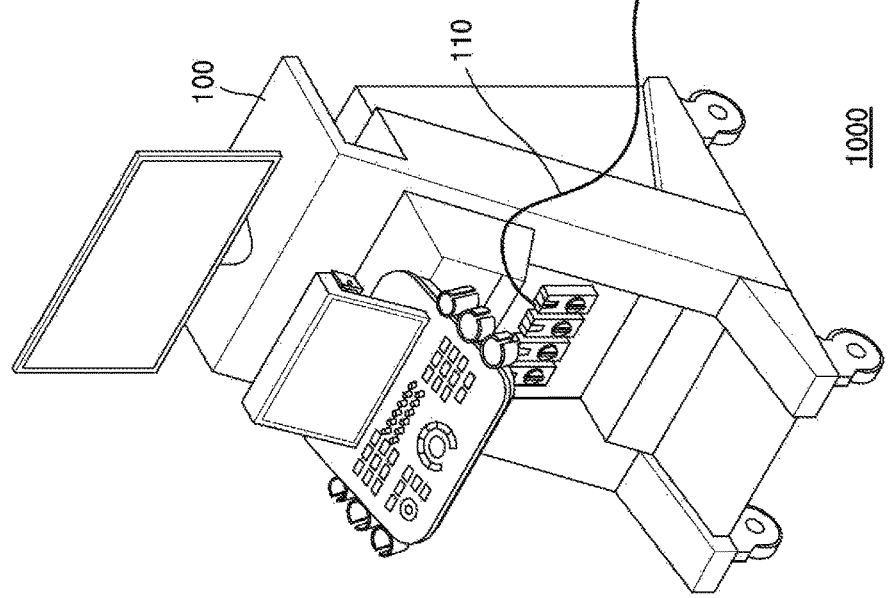

FIGS. 1A and 1B are diagrams showing examples of ultrasound diagnosis systems 1000 and 1001 according to embodiments.

Referring to FIG. 1A, in the ultrasound diagnosis system 1000, a wired probe 20 may be connected by wire to an ultrasound imaging apparatus 100. In other words, the wired probe 20 for transmitting and receiving ultrasound waves may be connected to a main body of the ultrasound diagnosis system 1000, i. e., the ultrasound imaging apparatus 100 via a cable 110.

Referring to FIG. 1B, in the ultrasound diagnosis system 1001, a wireless probe 20 may be connected wirelessly to an ultrasound imaging apparatus 210. In other words, the wireless probe 20 may be connected to the ultrasound imaging apparatus 210 via the same wireless network. For example, the wireless probe 20 and the ultrasound imaging apparatus 210 may be combined with a Millimeter Wave (mmWave) based wireless network, and the wireless probe 20 may transmit echo signals received through transducers to the ultrasound imaging apparatus 210 in the 60 GHz frequency band. The ultrasound imaging apparatus 210 may generate ultrasound images via various imaging modalities by using echo signals received in the 60 GHz frequency band and display the generated ultrasound images. In this case, the mmWave based wireless network may use a wireless communication method compliant with the WiGig standard developed by Wireless Gigabit Alliance (WGA), but is not limited thereto.

Figure 2:
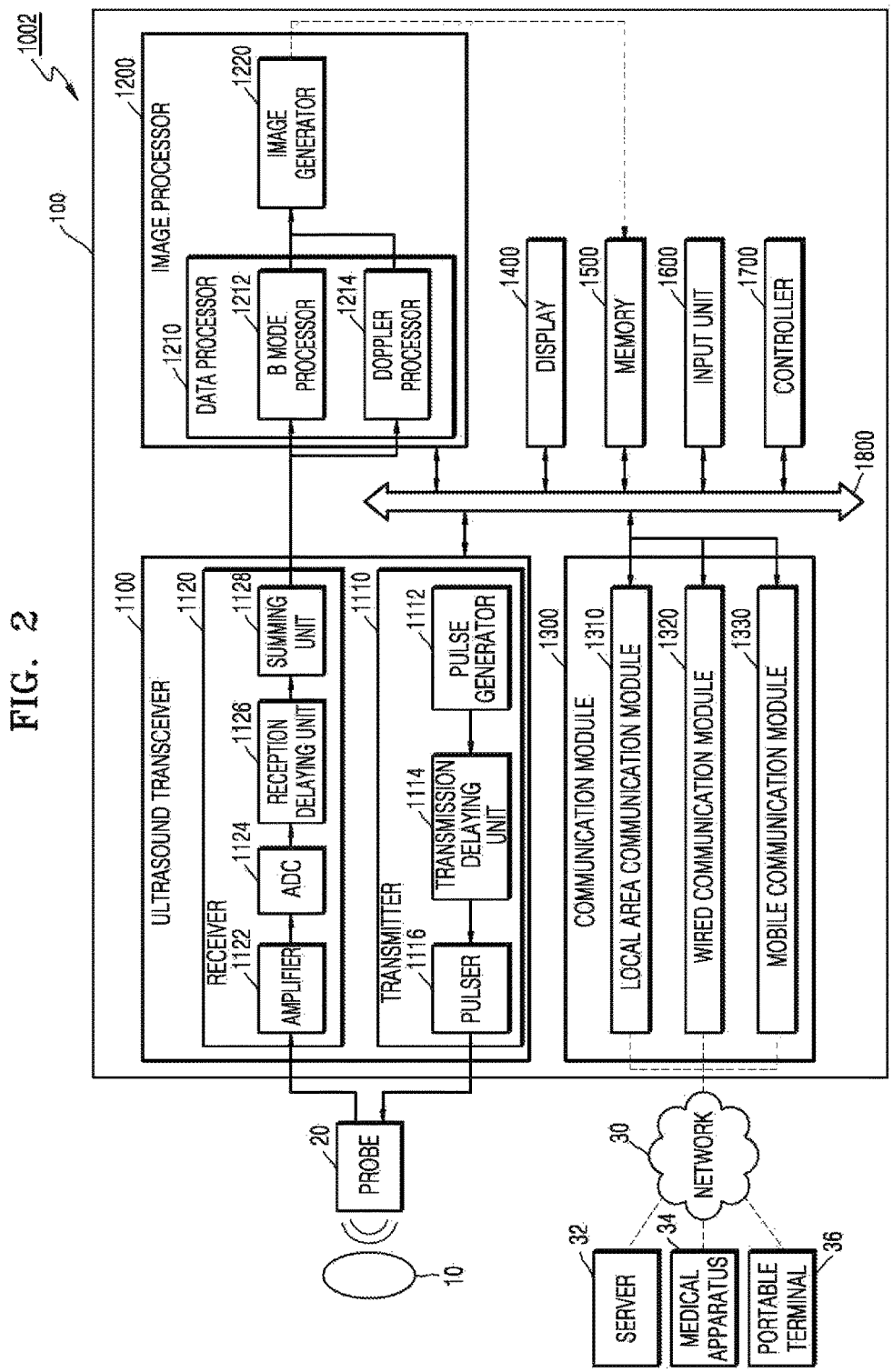
FIG. 2 is a block diagram of a configuration of an ultrasound diagnosis system according to an embodiment.

FIG. 2 is a block diagram of a configuration of an ultrasound diagnosis system 1002 according to an embodiment.

Referring to FIG. 2, the ultrasound diagnosis system 1002 may include a probe 20 and an ultrasound imaging apparatus 100. Referring to FIG. 1, the ultrasound imaging apparatus 100 may include a probe 20, an ultrasound transceiver 1100, an image processor 1200, a communication module 1300, a display unit 1400, a memory 1500, an input unit 1600, and a controller 1700, which may be connected to one another via buses 1800.

The ultrasound diagnosis system 1002 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound signals to an object 10 (or to an ROI in the object 10) in response to a driving signal applied by the ultrasound transceiver 1100 and receives echo signals reflected by the object 10 (or by the ROI in the object 10). The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis system 1002 by wire or wirelessly, and according to embodiments, the ultrasound diagnosis system 1002 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound imaging apparatus 1002 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. Furthermore, when the probe 20 is connected to the ultrasound imaging apparatus 1002 via a wireless network, the communication module 1300 may communicate with the probe 20.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object 10, such as ultrasound data and an ultrasound image that are input or output, and may also store algorithms or programs which are to be executed in the ultrasound imaging apparatus 1002.

Furthermore, the memory 1500 may store a plurality of previously generated body markers and a body marker generated by the controller 1700.

The input unit 1600 refers to a means via which a user inputs data for controlling the ultrasound imaging apparatus 1002. For example, the input unit 1600 may include hardware components, such as a keyboard, a mouse, a touch pad, a touch screen, and a jog switch, and software modules for operating the hardware components. However, embodiments are not limited thereto, and the input unit 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

Furthermore, the input unit 1600 receives a user input for selecting one from among a plurality of body markers prestored in the memory 1500.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input unit 1600 shown in FIG. 1.

All or some of the probe 20, the ultrasound transceiver 1100, the image processor 1200, the communication module 1300, the display 1400, the memory 1500, the input unit 1600, and the controller 1700 may be implemented as software modules. Furthermore, at least one selected from the ultrasound transceiver 1100, the image processor 1200, and the communication module 1300 may be included in the controller 1600. However, embodiments of the present invention are not limited thereto.

Figure 3:
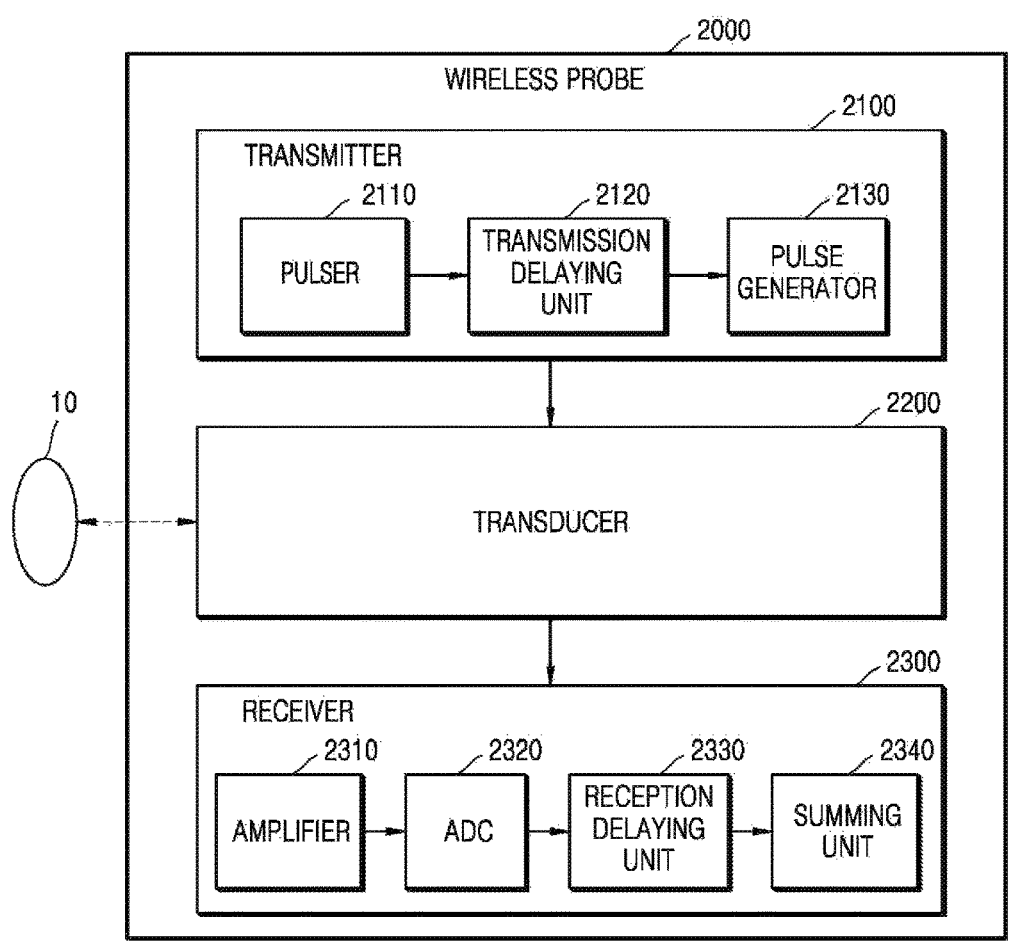
FIG. 3 is a block diagram of a configuration of a wireless probe according to an embodiment.

FIG. 3 is a block diagram of a wireless probe 2000 according to an embodiment.

As described above with reference to FIG. 3, the wireless probe 2000 may include a plurality of transducers, and, according to embodiments, may include some or all of the components of the ultrasound transceiver 1100 shown in FIG. 2.

The wireless probe 2000 according to the embodiment shown in FIG. 3 includes a transmitter 2100, a transducer 2200, and a receiver 2300. Since descriptions thereof are given above with reference to FIG. 2, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound imaging apparatus 1002 shown in FIG. 2.

Figure 4A:
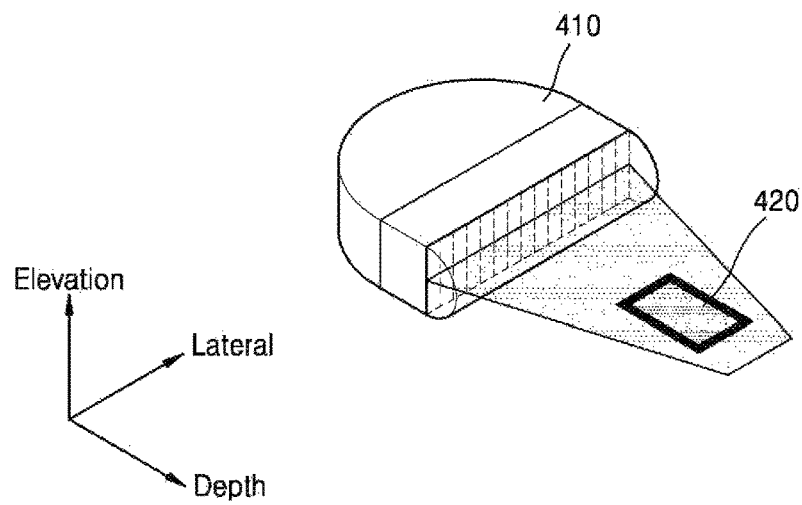
FIGS. 4A and 4B illustrate examples of one-dimensional (1D) and two-dimensional (2D) probes according to embodiments.
Figure 4B:
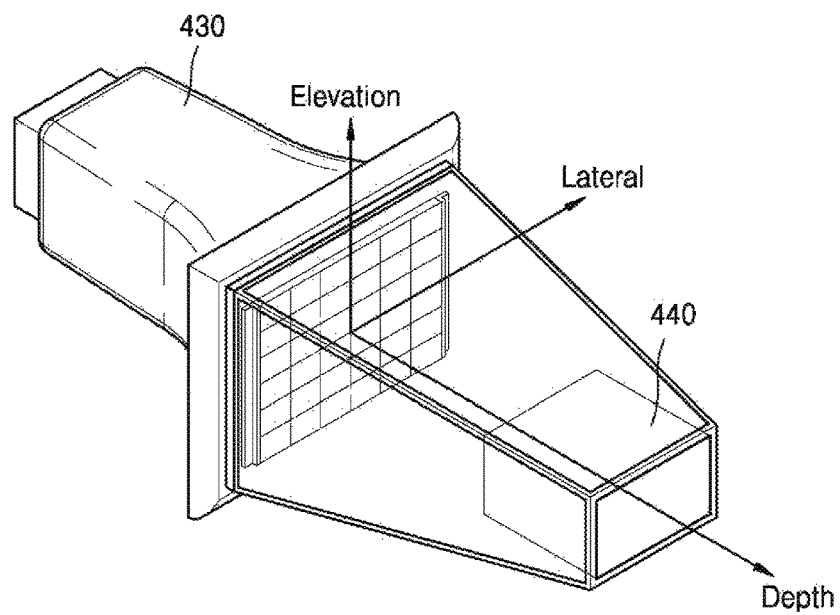

FIGS. 4A and 4B illustrate examples of one-dimensional (1D) and two-dimensional (2D) probes 410 and 430 according to embodiments.

The 1D probe 410 shown in FIG. 4A and the 2D probe 430 shown in FIG. 4B may respectively correspond to the wired probe 20 described with reference to FIG. 1A and the wireless probe 20 (or 2000) described with reference to FIG. 1B or 3.

Referring to FIG. 4A, the 1D probe 410 may be formed by a 1D array of a plurality of transducers. In this case, the transducers are elements constituting the 1D probe 410 and transmit ultrasound signals to an object 420 and receive echo signals reflected from the object 420. The plurality of transducers oscillate In response to reflected echo signals, generate electrical pulses corresponding to the oscillations, and output the electrical pulses to the ultrasound transceiver 1100.

Furthermore, transducers in the 1D probe 410 may constitute an aperture or sub-array. In this case, the aperture is a set of some of the plurality of transducers in the probe 410. The number of transducers that constitute an aperture is not limited to a specific number, and one aperture may be composed of a single transducer.

Furthermore, referring to FIG. 4B, the 2D probe 430 may be formed by a 2D array of a plurality of transducers. The 2D probe 430 may transmit ultrasound signals to a 3D object 440 and receive echo signals reflected from the object 440. In this case, the 2D probe 430 may transmit ultrasound signals to the object 440 and receive echo signals in the same manner as described with reference to FIG. 4A.

Figure 5:
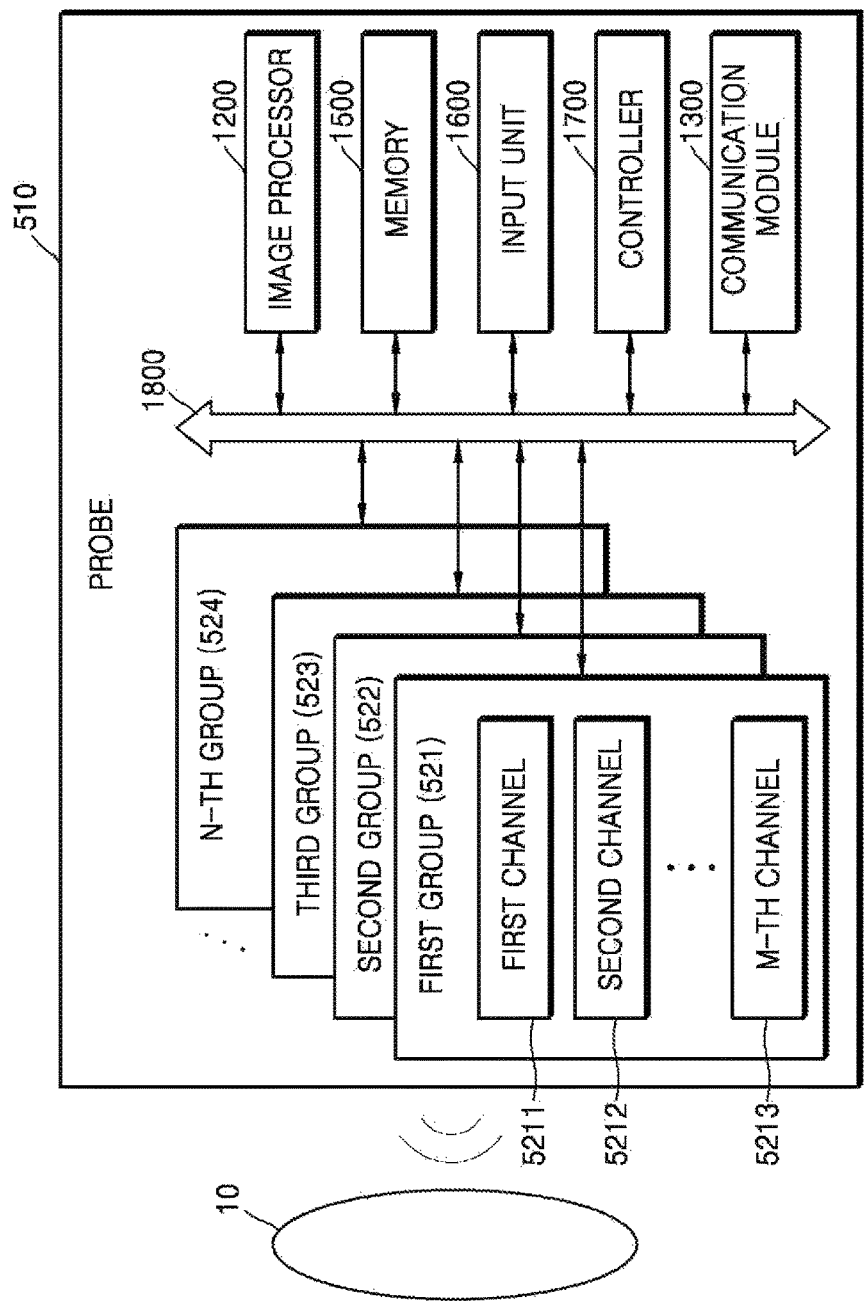
FIG. 5 illustrates a configuration of a probe according to an embodiment.

FIG. 5 illustrates a configuration of a probe 510 according to an embodiment.

The probe 510 of FIG. 5 may correspond to the 1D probe 410 described with reference to FIG. 4A or the 2D probe 430 described with reference to FIG. 4B.

The probe 510 transmits ultrasound signals to an object 10 (or to an ROI in the object 10) and receives echo signals reflected from the object 10 (or from the ROI in the object 10). Furthermore, the probe 510 may generate an ultrasound image by using ultrasound data corresponding to echo signals. In other words, the probe 510 may include the image processor 1200, the memory 1500, the input unit 1600, the controller 1700, and the communication module 1300 described with reference to FIG. 2, all of which may be connected to one another via the buses 1800.

The probe 510 includes a plurality of transducers, and the plurality of transducers oscillate in response to electric signals, generate acoustic energy, i.e., ultrasound waves, and receives echo signals reflected by the object 10 (or by the ROI in the object 10). In this case, each transducer is used to form a single channel, and may transmit an ultrasound signal and receive an echo signal according to an operation of an ultrasound transceiver included in each channel. In other words, each channel may include the ultrasound transceiver 1100 described with reference to FIG. 2.

Furthermore, a plurality of channels are classified into a predetermined number of groups 521 through 524. In other words, a first group 521 may include a plurality of channels 5211 through 5213. The probe 510 may include the plurality of groups 521 through 524. Thus, signals generated by the plurality of channels 5211 through 5213 in the first group 521 may be summed before being transmitted to the image processor 1200.

An example in which the probe 510 includes the plurality of groups 521 through 523, each group including the plurality of channels 5211 through 5213, will now be described in detail with reference to FIG. 6.

Figure 6:
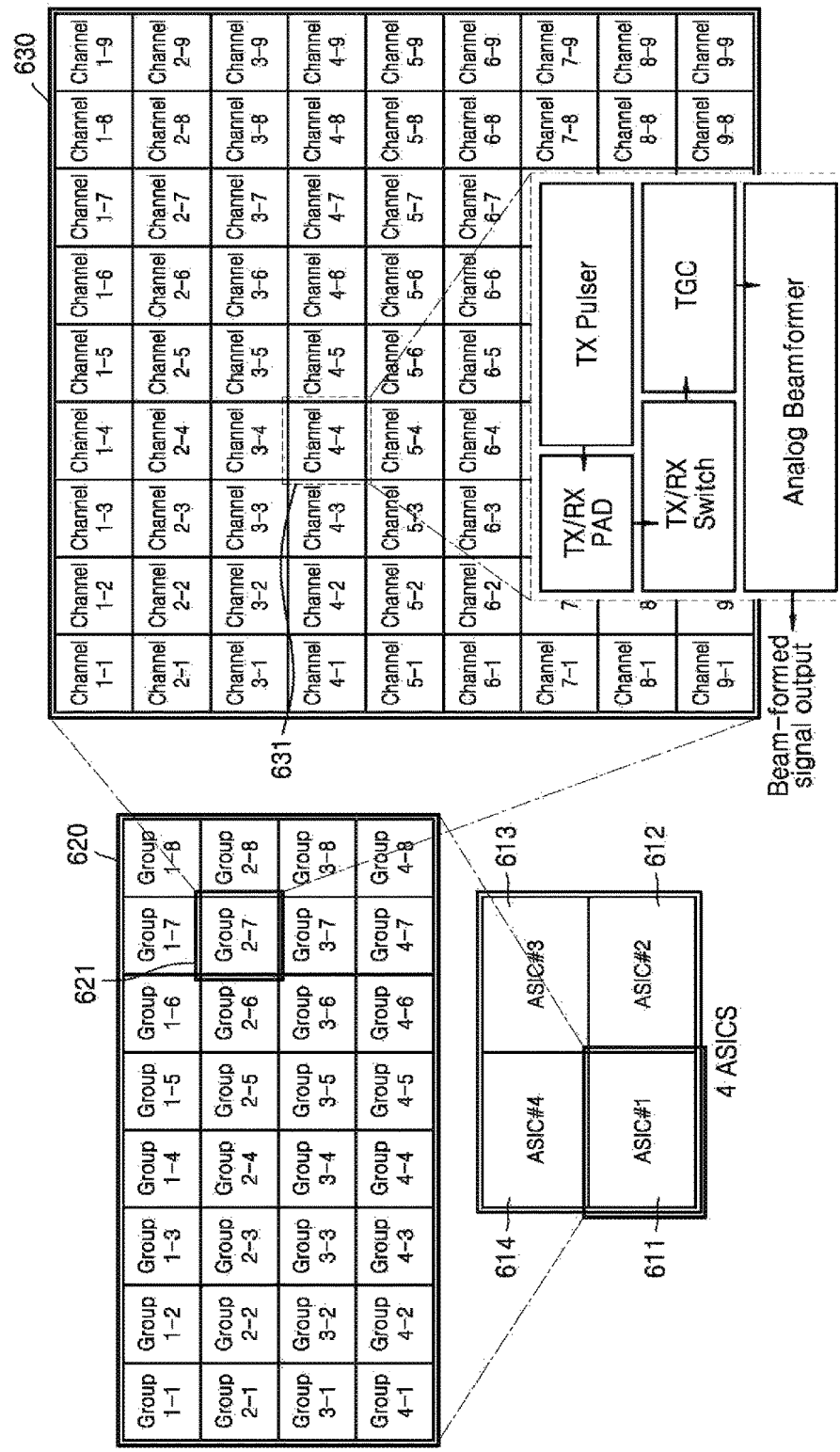
FIG. 6 is a diagram for explaining an example of groups and channels in each group according to an embodiment.

FIG. 6 is a diagram for explaining an example of groups and channels in each group according to an embodiment.

Referring to FIG. 6, a probe may include a plurality of Application Specific Integrated Circuits (ASICs) 611 through 614, and one ASIC 611 may include a plurality of groups 620. While FIG. 6 shows that one ASIC 611 includes thirty-two (32) groups 620, the number of groups in the ASIC 611 is not limited to 32. The ASIC 611 outputs one output signal by beamforming signals output from the groups 620.

Furthermore, one group 621 may include a plurality of channels 630. Although FIG. 6 shows that the group 621 includes eighty-one (81) channels 630, the number of channels is not limited to 81. Thus, the ASIC 611 may include a plurality of channels.

One channel 631 corresponds to one transducer. In detail, the channel 631 generates transmission ultrasound waves transmitted by one transducer, processes echo signals received by the transducer, and produces ultrasound data corresponding to the echo signals.

In other words, the channel 631 generates pulses for producing transmission ultrasound waves based on a PRF and delays the pulses by delay times necessary for determining transmission directionality. The channel 631 also applies a driving signal (or a driving pulse) to its corresponding transducer. For example, the channel 631 may include the transmitter 1110 described with reference to FIG. 2.

Furthermore, the channel 631 amplifies echo signals received from the transducer and performs analog-to-digital conversion (ADC) with respect to the amplified echo signals. The channel 631 may selectively perform time gain compensation (TGC) on digital echo signals. The channel 631 also delays the digital echo signals by delay times necessary for determining reception directionality to thereby generate ultrasound data. For example, the channel 631 may include the receiver 1120 described with reference to FIG. 2.

As described above with reference to FIGS. 1 through 6, the probe may include a plurality of channels, each channel corresponding to a single transducer. Thus, when a leakage current occurs due to a fault in a transducer or internal circuitry of a channel, the probe may not operate normally. Examples in which an electronic circuit included in a probe (hereinafter, referred to as an "electronic circuit") checks whether a leakage current has occurred in a channel and controls an operation of the channel if it is determined that the leakage current has occurred will be described in detail below with reference to FIGS. 7 through 15.

While FIGS. 7 through 15 show that the electronic circuit checks whether a leakage current has occurred in a single channel 631 and controls an operation of the channel 631, embodiments are not limited thereto. In other words, the electronic circuit may check whether a leakage current has flowed into the group 621 or the ASIC 611 and control an operation of the group 621 or the ASIC 611. Furthermore, the electronic circuit may check whether a leakage current has occurred in the probe (510 of FIG. 5) and control an operation of the probe 510.

As one example, the electronic circuit may check whether a leakage current has flowed into the group 621 and control an operation of the group 621 based on a result of the checking. For example, if the leakage current flows into the group 621, the electronic circuit may block the flow of current into the group 621, block the flow of current into at least one element included in the group 621, or block output of a signal generated by the group 621.

As another example, the electronic circuit may control an operation of the ASIC 611 based on whether a leakage current has flowed into the ASIC 611. For example, if the leakage current flows into the ASIC 611, the electronic circuit may block the flow of current into the ASIC 611, block the flow of current into at least one element included in the ASIC 611, or block output of a signal generated by the ASIC 611.

As another example, the electronic circuit may control an operation of the probe 510 based on whether a leakage current has flowed into the probe 510. For example, if the leakage current flows into the probe 510, the electronic circuit may block the flow of current into the probe 510, block the flow of current into at least one element included in the probe 519, or block output of a signal generated by the probe 510.

Functions of the electronic circuit as will be described below with reference to FIGS. 7 through 15 may be performed by a processor included in the probe 510. The processor may be implemented as an array of a plurality of logic gates or a combination of a general purpose microprocessor and a program that can be run on the general purpose microprocessor. Furthermore, it will be appreciated by those of ordinary skill in the art to which the embodiment pertains that the processor may be formed using different types of hardware.

For example, the processor may check whether a leakage current has flowed into the channel 631, the group 621, the ASIC 611, or the probe 510 and control an operation of the channel 631, the group 621, the ASIC 611, or the probe 510 based on a result of the checking.

Figure 7:
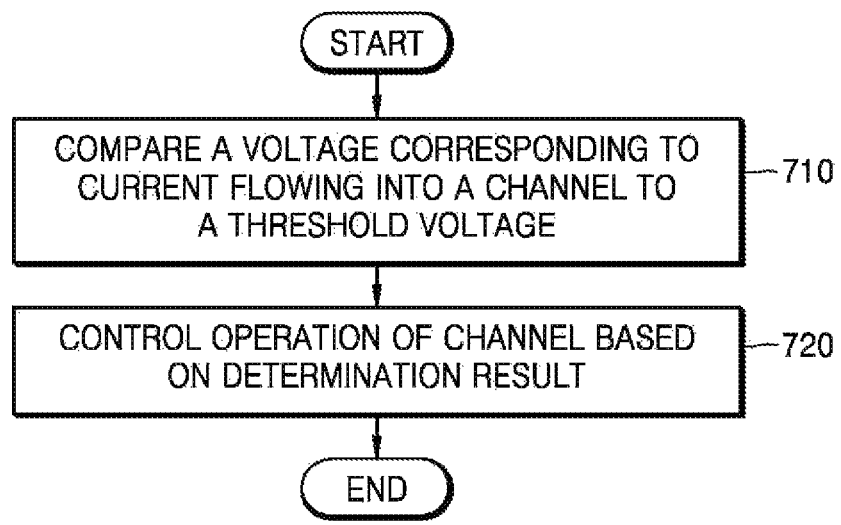
FIG. 7 is a flowchart of a method of operating an electronic circuit according to an embodiment.

FIG. 7 is a flowchart of a method of operating an electronic circuit according to an embodiment.

The electronic circuit compares a voltage corresponding to current flowing into a channel to a threshold voltage (operation 710). That is, the electronic circuit compares the voltage corresponding to the current flowing into the channel to the threshold voltage to determine an occurrence of an abnormal current by using the voltage corresponding to the current flowing into the channel. For example, the electronic circuit may convert the current flowing into the channel into the voltage corresponding to the current and determine the occurrence of an abnormal current in the channel based on a result of the comparing of the voltage to the threshold voltage. In this case, determining occurrence of an abnormal current in a channel means determining whether a leakage current is flowing into the channel. For example, if a voltage obtained by converting current flowing into a channel exceeds a threshold voltage, the electronic circuit may determine whether the leakage current is flowing into the channel.

The electronic circuit controls an operation of the channel based on a result of the comparing (operation 720). In detail, when a leakage current does not flow into the channel, the electronic circuit does not operate. In other words, when the leakage current does not flow into the channel, the electronic circuit does not affect an operation of the channel at all.

On the other hand, when a leakage current flows into the channel, the electronic circuit may control the operation of the channel in various ways. As one example, the electronic circuit may block the flow of current into the channel. As another example, the electronic circuit may block the flow of current into at least one element included in the channel. As another example, the electronic circuit may block output of a signal generated by the channel. In this case, the signal generated by the channel means a signal corresponding to ultrasound data generated for the channel.

In other words, when the leakage current flows into the channel, the electronic circuit controls the channel not to operate normally. Thus, it is possible to prevent a malfunction of the channel within a probe or failure of the probe due to the occurrence of the leakage current.

Furthermore, although not shown in FIG. 7, the electronic circuit may generate a signal notifying that a leakage current has flowed into a channel (hereinafter, referred to as a 'notification signal'). In other words, when the leakage current flows into the channel, the electronic circuit may generate a notification signal, and the probe may output the notification signal. For example, the notification signal may be a signal indicated by a lamp in the probe, such as a light-emitting diode (LED) lamp, flashing on or off, or a vibration signal generated by the probe.

An example in which an electronic circuit is included in a probe will now be described in detail with reference to FIG. 8.

Figure 8:
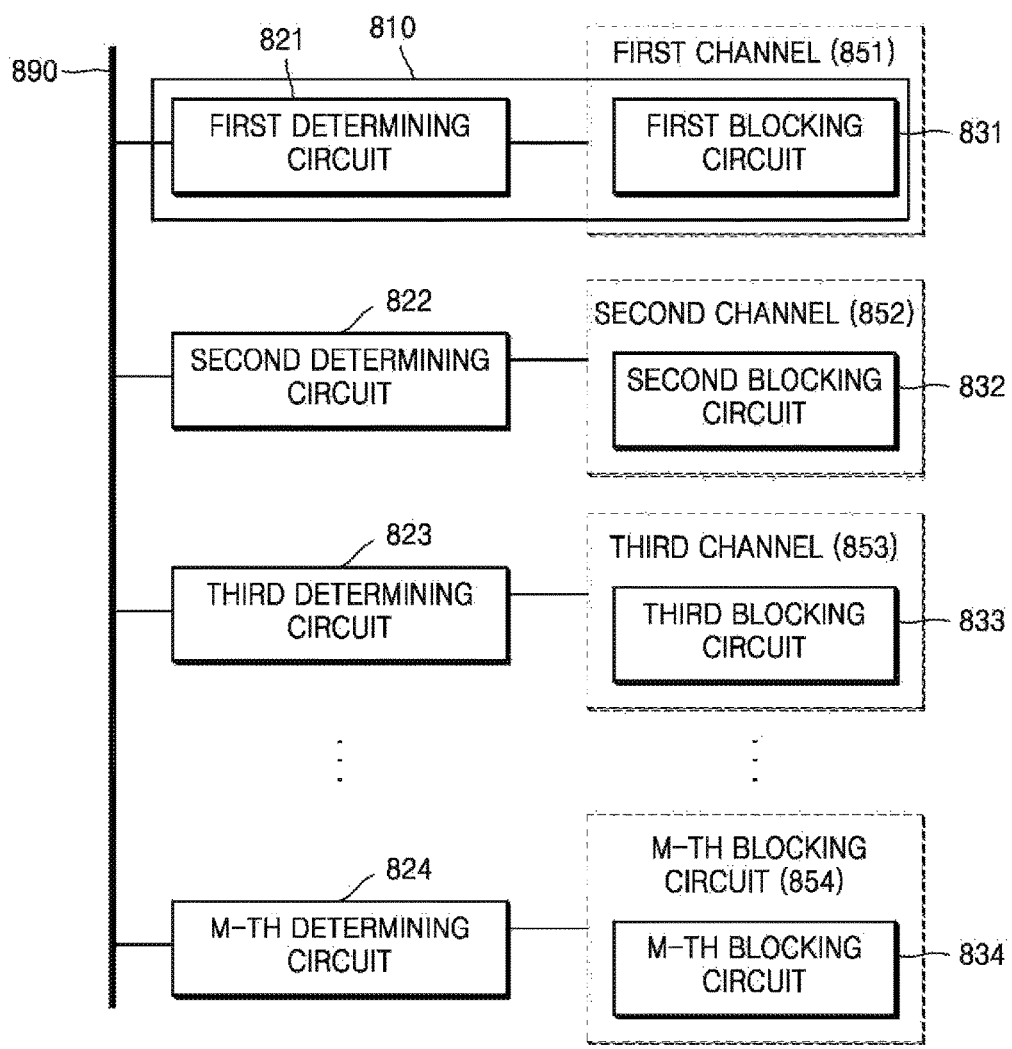
FIG. 8 illustrates an example of a configuration in which electronic circuits are included in a probe according to an embodiment.

FIG. 8 is a diagram for explaining an example of a configuration in which electronic circuits are included in a probe according to an embodiment.

FIG. 8 illustrates an example in which electronic circuits 810 are respectively connected to a plurality of channels 851 through 854. One electronic circuit 810 includes a first determining circuit 821 and a first blocking circuit 831, and is connected to a first channel 851. Thus, when the probe includes the plurality of channels 851 through 854, the probe may also include a corresponding number of electronic circuits 810.

Furthermore, as shown in FIG. 8, the first determining circuit 821 may be connected between the first channel 851 and a conductive wire 890 for supplying current to the channel 851. Thus, the first determining circuit 821 may determine whether the current flowing into the first channel 851 is an abnormal current. In other words, the first determining circuit 821 may check whether a leakage current is included in the current flowing into the first channel 851.

An example of the first determining circuit 821 will now be described in detail with reference to FIGS. 9 and 10.

Figure 9:
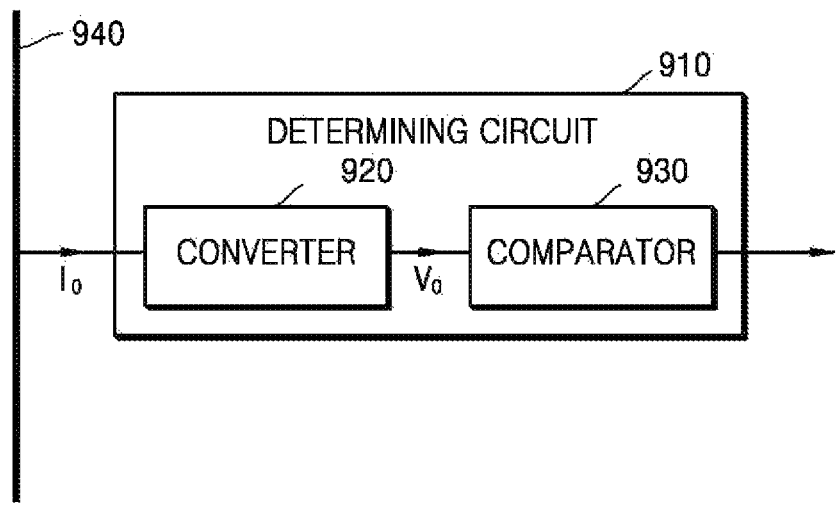
FIG. 9 is a block diagram of a configuration of a determining circuit according to an embodiment.

FIG. 9 is a block diagram of a configuration of a determining circuit 910 according to an embodiment.

Referring to FIG. 9, the determining circuit 910 includes a converter 920 and a comparator 930.

The converter 920 converts current $I_0$ flowing from a conductive wire 940 into voltage $V_0$. In detail, the converter 920 converts the current $I_0$ flowing from the conductive wire 940 into its corresponding voltage $V_0$.

The comparator 930 compares the voltage $V_0$ to a threshold voltage. In detail, the comparator 930 generates an output signal based on whether the voltage $V_0$ exceeds the threshold voltage. For example, if the voltage $V_0$ does not exceed the threshold voltage, the comparator 930 may not generate an output signal. On the other hand, if the voltage $V_0$ exceeds the threshold voltage, the comparator 930 may generate an output signal. The output signal generated by the comparator 930 may then be transmitted to the blocking circuit 831, 832, 833, or 834 of FIG. 8 and be used as a signal notifying the blocking circuit 831, 832, 833, or 834 about starting an operation thereof.

In addition, while FIG. 9 shows that the determining circuit 910 includes the converter 920, embodiments are not limited thereto. In other words, without converting the current $I_0$ flowing from the conductive wire 940 into the voltage $V_0$, the comparator 930 may directly generate an output signal based on whether the current $I_0$ exceeds a threshold current.

Figure 10:
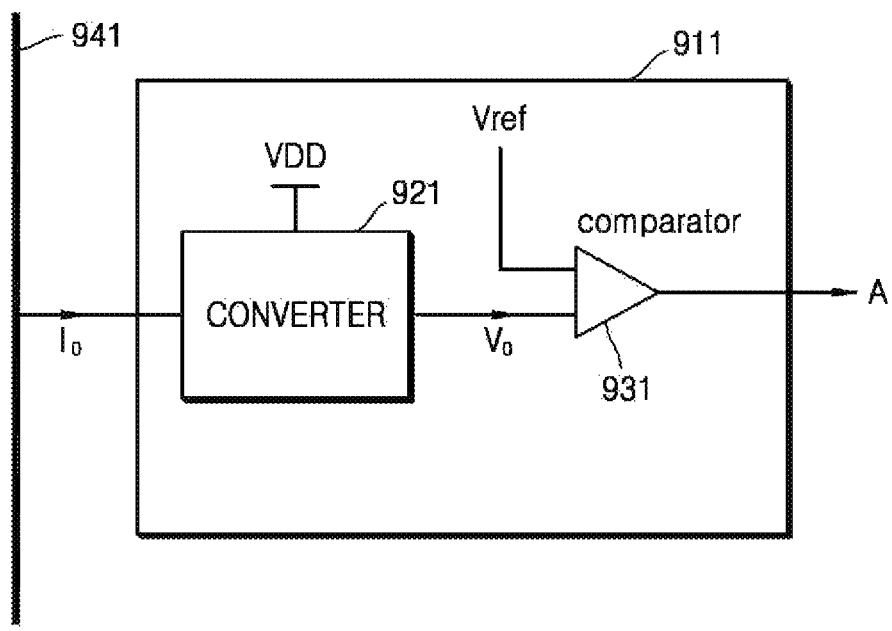
FIG. 10 is a diagram for explaining an example of a determining circuit according to an embodiment.

FIG. 10 is a diagram for explaining an example of a determining circuit 911 according to an embodiment.

Referring to FIG. 10, the determining circuit 911 includes a current-to-voltage (I-V) converter 921 and a comparator 931. While FIG. 10 shows the I-V converter 921 implemented as an example of the converter 920 and the comparator 931 implemented as an example of the comparator 930, embodiments are not limited thereto. In other words, the I-V converter 921 and the comparator 930 are not limited thereto and may be any other devices as long as they can perform the same operations of the I-V converter 921 and the comparator 931 as described with reference to FIG. 9.

Furthermore, although FIG. 10 shows that the determining circuit 911 includes only the I-V converter 921 and the comparator 931, embodiments are not limited thereto. In other words, the determining circuit 911 may further include other devices necessary for operations of the I-V converter 921 and the comparator 931 and a conductive wire.

The I-V converter 921 converts current $I_0$ fed from a conductive wire 941 into voltage $V_0$. In detail, the I-V converter 921 operates as an operating voltage VDD is applied thereto and converts the current $I_0$ fed from the conductive wire 941 into the voltage $V_0$.

The comparator 931 compares the voltage $V_0$ to a threshold voltage Vref and generates an output signal A based on a result of the comparing. For example, if the voltage $V_0$ exceeds the threshold voltage Vref, the comparator 931 may generate the output signal A. The output signal A generated by the comparator 931 may be used as a signal for notifying the blocking circuit 831, 832, 833, or 834 about starting an operation thereof.

Referring back to FIG. 8, the first blocking circuit 831 is connected to the first determining circuit 821. While FIG. 8 shows that the first blocking circuit 831 is included in the first channel 851, embodiments are not limited thereto. In other words, the first blocking circuit 831 may be disposed outside the first channel 851. The first blocking circuit 831 may receive an output signal of the first determining circuit 821 to control operations of devices included in the first channel 851.

An example of the first blocking circuit 831 according to an embodiment will now be described with reference to FIGS. 11 and 12.

Figure 11:
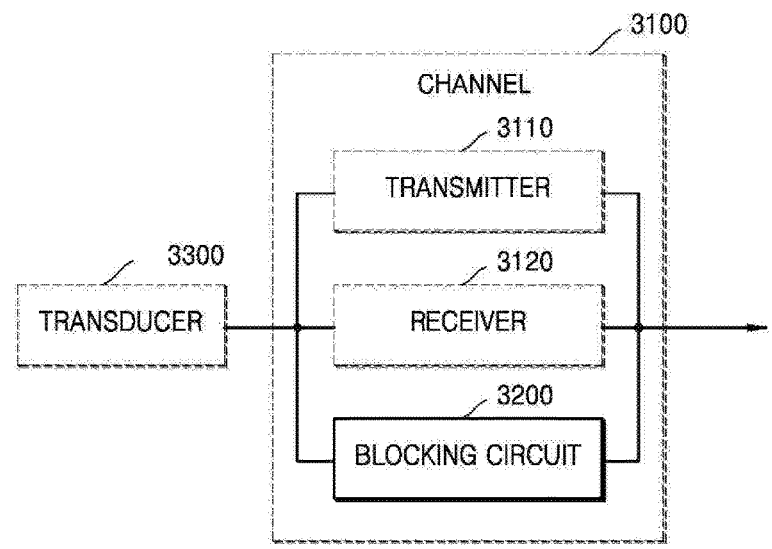
FIG. 11 is a block diagram of a configuration of a blocking circuit according to an embodiment.

FIG. 11 is a block diagram of a configuration of an example of a blocking circuit 3200 according to an embodiment.

Referring to FIG. 11, a channel 3100 is coupled to a transducer 3300. Furthermore, the channel 3100 includes a transmitter 3110 and a receiver 3120, and the blocking circuit 3200 is disposed inside the channel 3100 and is connected to the transmitter 3110 and the receiver 3120.

As described above with reference to FIG. 10, the blocking circuit 3200 may also be disposed outside the channel 3100. However, even when the blocking circuit 3200 is disposed outside the channel 3100, the blocking circuit 3200 needs to be connected to the transmitter 3110 and the receiver 3120 in order to control operations of devices included in the channel 3100.

When it is determined that a leakage current is present in current flowing into the channel 3100, the blocking circuit 3200 controls an operation of the channel 3100. In detail, when the leakage current does not flow into the channel 3100, the blocking circuit 3200 does not operate. In other words, when the leakage current does not flow into the channel 3100, the blocking circuit 3200 does not affect an operation of the channel 3100 at all.

On the other hand, when a leakage current flows into the channel 3100, the blocking circuit 3200 may control the operation of the channel 3100 in various ways. As one example, the blocking circuit 3200 may block the flow of current into the channel 3100. As another example, the blocking circuit 3200 may block the flow of current into at least one element included in the channel 3100. In other words, the blocking circuit 3200 may block the flow of current into elements respectively included in the transmitter 3110 and the receiver 3120. As another example, the blocking circuit 3200 may block a signal generated by the channel 3100 from being output. The signal generated by the channel 3100 means a signal corresponding to ultrasound data generated for the channel. In detail, the blocking circuit 3200 may block ultrasound data generated by the receiver 3120 from being output to outside the channel 3100.

In other words, when a leakage current flows into the channel 3100, the blocking circuit 3200 controls the channel 3100 not to operate normally. Thus, it is possible to prevent malfunction of the channel within a probe or failure of the probe due to occurrence of the leakage current.

Figure 12:
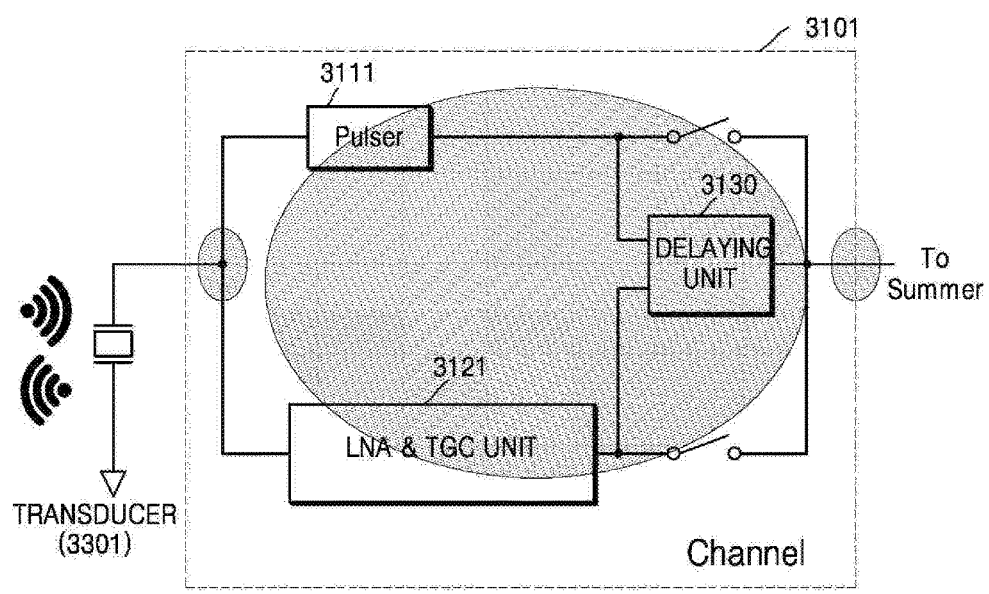
FIG. 12 is a diagram for explaining an example of a blocking circuit according to an embodiment.

FIG. 12 is a diagram for explaining an example of a channel 3101 and the blocking circuit (3200 of FIG. 11) according to an embodiment.

Referring to FIG. 12, the channel 3101 includes a pulser 3111, a low noise amplifier (LNA) & time gain compensator (TGC) 3121, and a delaying unit 3130. In this case, the pulser 3111 and the LNA & TGC unit 3121 are components respectively representing the transmitter (3110 of FIG. 11) and the receiver (3120 of FIG. 11). In other words, the transmitter 3110 may further include components, other than the pulser 3111, necessary to perform the operations of the transmitter (1110 of FIG. 2) described with reference to FIG. 2. Furthermore, the receiver 3120 may further include components, other than the LNA & TGC unit 3121, necessary to perform the operations of the receiver (1120 of FIG. 2) described with reference to FIG. 2.

Furthermore, the channel 3101 includes the delaying unit 3130 configured to delay pulses by delay times necessary for determining transmission directionality and delay digital echo signals by delay times necessary for determining reception directionality. In other words, the delaying unit 3130 may participate in operations of the transmitter 3110 and the receiver 3120. While FIG. 12 shows that the delaying unit 3130 is separate from the transmitter 3110 and the receiver 3120, embodiments are not limited thereto. For example, the transmitter 3110 and the receiver 3120 may each include the delaying unit 3130.

When a leakage current flows into the channel 3101, the blocking circuit 3200 may control the operation of the channel 3101 in various ways. As one example, the blocking circuit 3200 may block the flow of current into the channel 3101. As another example, the blocking circuit 3200 may block the flow of current into at least one element included in the channel 3101. In other words, the blocking circuit 3200 may block the flow of current into the pulser 3111 and the LNA & TGC unit 3121. As another example, the blocking circuit 3200 may block a signal generated by the channel 3101 from being output to outside the channel 3101.

Figure 13:
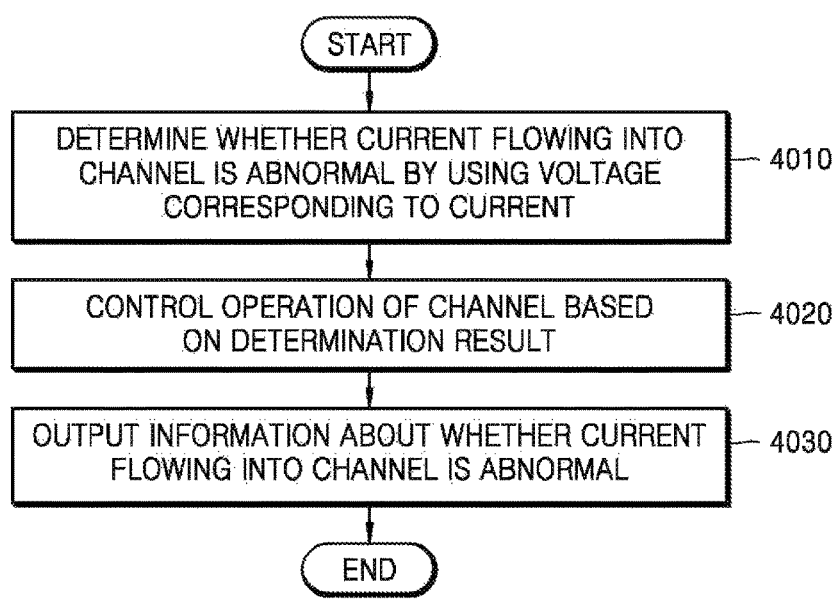
FIG. 13 is a flowchart of another example of a method of operating an electronic circuit according to an embodiment.

FIG. 13 is a flowchart of another example of a method of operating an electronic circuit according to an embodiment.

Since operations 4010 and 4020 shown in FIG. 13 respectively correspond to operations 710 and 720 described with reference to FIG. 7, detailed descriptions thereof will be omitted below.

An electronic circuit outputs information about whether current flowing into a channel is an abnormal current (operation 4030). In other words, the electronic circuit may output information about a channel into which an abnormal current (i.e., current containing a leakage current) has flowed to an external device.

As described above with reference to FIGS. 1 through 6, since a probe includes a plurality of channels, it is difficult to identify a channel into which a leakage current has flowed from among the plurality of channels. In particular, as described with reference to FIG. 5, when a plurality of channels are set to form a group and signals generated respectively by the plurality of channels in the group are added together before being transmitted to the outside, it is hard to determine a channel into which a leakage current has flowed.

In detail, the electronic circuit outputs to an external device the information about a channel into which an abnormal current has flowed from among a plurality of channels in a probe. An example in which the electronic circuit outputs information about a channel into which an abnormal current has flowed to an external device will now be described in more detail with reference to FIGS. 14 and 15.

Figure 14:
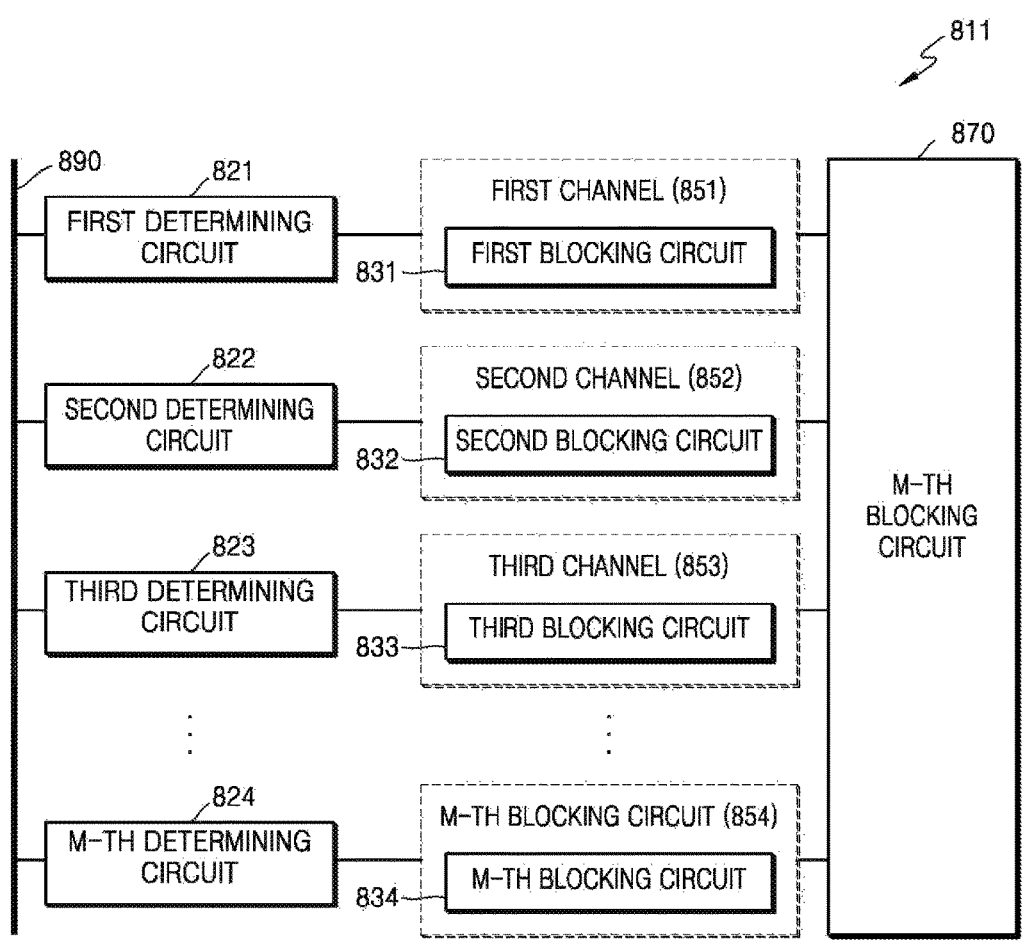
FIG. 14 illustrates another example of a configuration in which an electronic circuit is included in a probe according to an embodiment.

FIG. 14 illustrates another example of a configuration in which an electronic circuit is included in a probe according to an embodiment.

Referring to FIG. 14, an electronic circuit 811 includes first through M-th determining circuits 821 through 824, first through M-th blocking circuits 831 through 834, and a transmission circuit 870. Since the first through M-th determining circuits 821 through 824 and the first through M-th blocking circuits 831 through 834 perform the same operations as described with reference to FIGS. 7 through 12, detailed descriptions thereof will be omitted here.

The transmission circuit 870 identifies a channel into which an abnormal current has flowed from among first through M-th channels 851 through 854. The transmission circuit 870 also transmits information about the channel into which an abnormal current has flowed to the outside. The first through M-th determining circuits 821 through 824 respectively determine whether current flowing into the first through M-th channels 851 through 854 is an abnormal current, and one of the first through M-th determining circuits 821 through 824 connected to a channel into which the abnormal current has flowed generates the output signal A of FIG. 9. Thus, the transmission circuit 870 may identify, based on the output signal A generated by the determining circuit, a channel into which an abnormal current has flowed from among the first through M-th channels 851 through 854.

Figure 15:
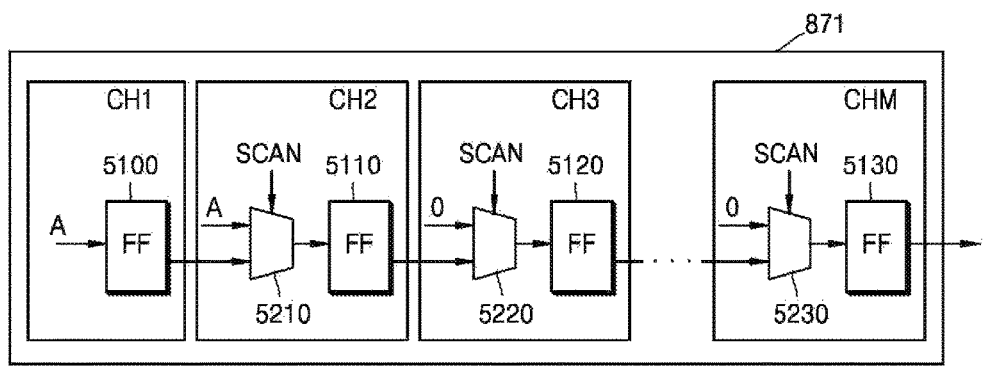
FIG. 15 is a diagram for explaining an example of a transmission circuit according to an embodiment.

FIG. 15 is a diagram for explaining an example of a transmission circuit 871 according to an embodiment.

Referring to FIG. 15, the transmission circuit 871 includes flip-flops 5100, 5110, 5120, and 5130 respectively connected to first through M-th channels CH1, CH2, CH3, and CHM. The transmission circuit 871 may further include multiplexers 5210, 5220, and 5230 that are respectively coupled to the first through M-th channels CH1, CH2, CH3, and CHM and receive information about a previous channel, information about a current channel, and a scan command. In this case, information about a channel means information about whether an abnormal current has flowed into the channel, and the scan command refers to a command requesting a search for a channel into which an abnormal current has flowed.

While FIG. 15 shows that the transmission circuit 871 includes only the flip-flops 5100, 5110, 5120, and 5130 and the multiplexers 5210, 5220, and 5230, embodiments are not limited thereto. In other words, the transmission circuit 871 may further include other devices necessary to operate the flip-flops 5100, 5110, 5120, and 5130 and the multiplexers 5210, 5220, and 5230 and a conductive wire.

The flip-flops 5100, 5110, 5120, and 5130 included in the transmission circuit 971 may be connected to one another. In other words, the flip-flops 5100, 5110, 5120, and 5130 respectively coupled to the first through M-th channels CH1, CH2, CH3, and CHM may be connected together to receive a signal A generated by a previous channel.

Signal A means a signal notifying that an abnormal current has flowed into a channel. For example, a channel into which an abnormal current has not flowed may not generate signal A but transmit a default value (e.g., 0) to a next channel.

If an abnormal current flows into the first channel CH1, data corresponding to signal A generated by a determining circuit of the first channel CH1 is fed into the flip-flop 5100. The flip-flop 5100 updates internal data by using the input data and transmits the updated data to the multiplexer 5210. If the abnormal current flows into a second channel CH2 as well, data corresponding to signal A generated by a determining circuit of the second channel CH2 is fed into the multiplexer 5210. The flip-flop 5110 updates internal data by using the data transmitted by the multiplexer 5210 and transmits the updated data to the multiplexer 5220. In this way, the transmission circuit 870 identifies the first and second channels CH1 and CH2 into which the abnormal current has flowed, from among the first through M-th channels CH1, CH2, CH3, and CHM, and then transmits information about the first and second channels CH1 and CH2 into which the abnormal current has flowed to an external device.

As described above, the electronic circuit controls a channel into which a leakage current has flowed not to operate normally. Thus, it is possible to prevent a malfunction of the channel within a probe or failure of the probe due to occurrence of the leakage current.

Furthermore, the electronic circuit transmits information about the channel into which the leakage current has flowed to an external device, thereby allowing the user to easily determine which channel has an abnormal current via a scan command.

The above methods according to the embodiments can be recorded in programs that can be executed on a computer and be implemented through general purpose digital computers which can run the programs using a non-transitory computer-readable recording medium. Data structures described in the above methods can also be recorded on a non-transitory computer-readable medium in a variety of ways, with examples of the medium including recording media, such as magnetic storage media (e.g., ROM, RAM, USB, floppy disks, hard disks, etc.) and optical recording media (e.g., CD-ROMs or DVDs).

While one or more embodiments have been described with reference to the figures, it will be understood by those of ordinary skill in the art that various changes in form and details may be made therein without departing from the spirit and scope of the inventive concept as defined by the following claims. Thus, it should be understood that the embodiments described therein should be considered in a descriptive sense only and not for purposes of limitation. The scope of the present inventive concept is defined not by the detailed description thereof but by the appended claims, and all differences within the scope of the appended claims and their equivalents will be construed as being included in the present inventive concept.

What is claimed is:

1. A method of controlling an operation of a channel including at least one transducer, the method comprising:
    comparing a voltage corresponding to current flowing into the channel to a threshold voltage;
    controlling the operation of the channel based on a result of the comparing; and
    outputting information about whether the current flowing into the channel is an abnormal current, the outputting of information being performed by a circuit comprising a flip-flop coupled to the channel and a flip-flop of a previous channel,
    wherein the outputting of information comprises:
        receiving, by the flip-flop, a signal from the flip-flop of the previous channel; and
        outputting, by flip-flop, information about whether the current flowing into the channel is an abnormal current based on the received signal and the result of the comparing .

2. The method of claim 1, wherein the controlling of the operation of the channel comprises blocking flow of the current into the channel.

3. The method of claim 1, wherein the controlling of the operation of the channel comprises blocking flow of the current into at least one element included in the channel.

4. The method of claim 1, wherein the controlling of the operation of the channel comprises blocking a signal generated by the channel from being output.

5. The method of claim 1, wherein the channel is included in a probe, and the probe comprises a two-dimensional (2D) transducer array.

6. The method of claim 1, wherein the comparing of the voltage comprises converting the current flowing into the channel into the voltage and comparing the voltage to the threshold voltage.

7. The method of claim 1, wherein the comparing of the voltage is performed by a circuit comprising a converter and a comparator.

8. A non-transitory computer-readable recording medium having recorded thereon a program for executing the method of claim 1 on a computer.

9. An apparatus for controlling an operation of a channel including at least one transducer, the apparatus comprising:
    a first circuit configured to compare a voltage corresponding to current flowing into the channel to a threshold voltage;
    a second circuit configured to control the operation of the channel based on a result of the comparing; and
    a flip-flop coupled to the channel and a flip-flop of a previous channel,
    wherein the flip-flop outputs information about whether the current flowing into the channel is an abnormal current based on a received signal from the flip-flop of the previous channel and the result of the comparing.

10. The apparatus of claim 9, wherein the first circuit is further configured to convert the current flowing into the channel into the voltage and compare the voltage to the threshold voltage.

11. The apparatus of claim 9, wherein the first circuit comprises a converter and a comparator.

12. The apparatus of claim 9, wherein the second circuit is further configured to block flow of the current into the channel.

13. The apparatus of claim 9, wherein the second circuit is further configured to block flow of the current into at least one element included in the channel.

14. The apparatus of claim 9, wherein the second circuit is further configured to block output of a signal generated by the channel.

15. The apparatus of claim 9, wherein the channel is included in a probe, and the probe comprises a two-dimensional (2D) transducer array.

16. A probe connected to an ultrasound diagnosis apparatus, the probe comprising a control circuit that is connected to channels, each channel including a group of transducers in the probe, wherein the control circuit comprises:
a first circuit configured to compare a voltage corresponding to current flowing into a channel to a threshold voltage;
a second circuit configured to control an operation of the channel based on a result of the comparing; and
a flip-flop coupled to the channel and a flip-flop of a previous channel,
wherein the flip-flop outputs information about whether the current flowing into the channel is an abnormal current based on a received signal from the flip-flop of the previous channel and the result of the comparing.

\* \* \* \* \*